US005509898A

United States Patent [19]

Isono et al.

[11] Patent Number: 5,509,898

[45] Date of Patent: Apr. 23, 1996

[54] CONTAINER FOR THERAPEUTIC USE

[75] Inventors: Keinosuke Isono, Kawaguchi; Tatsuo Suzuki, Machida, both of Japan

[73] Assignee: Material Engineering Technology Laboratory, Inc., Tokyo, Japan

[21] Appl. No.: 239,133

[22] Filed: May 6, 1994

[30] Foreign Application Priority Data

May 10, 1993 [JP] Japan .................................... 5-132729
May 12, 1993 [JP] Japan .................................... 5-133836

[51] Int. Cl.[6] .................................................... A61M 37/00

[52] U.S. Cl. ............................ 604/87; 604/410; 604/416; 206/219; 206/222; 222/94; 128/DIG. 24

[58] Field of Search .................................... 604/403, 408, 604/410, 416, 56, 82, 87, 88, 89, 91; 128/DIG. 24; 222/94; 206/219, 222

[56] References Cited

U.S. PATENT DOCUMENTS 4,403,992 9/1983 Bertellini et al. ...................... 604/82 X
4,548,606 10/1985 Larkin .
4,576,603 3/1986 Moss ........................................ 604/410
5,263,929 11/1993 Falcone et al. ........................... 604/89

FOREIGN PATENT DOCUMENTS 0092528 10/1983 European Pat. Off. .
2369181 5/1978 France .
WO83/01569 5/1983 WIPO .

*Primary Examiner*—Mary Beth Jones
*Attorney, Agent, or Firm*—Oblon, Spivak, McClelland, Maier & Neustadt

[57] ABSTRACT

A therapeutic container is provided for use in a closed therapy system. The therapeutic container is a flexible container that has suspending means, that is divided into a first compartment and a second compartment by an isolation zone, that has an outlet member provided with an openable communication passage which permits communication between the first and second compartments, and that optionally has a second openable communication passage at a location proximal to the end of the container on the side of the suspending means, whereby both the contents of the first and the second compartments can be discharged through the outlet member at a constant mixing ratio while mixing them together.

6 Claims, 7 Drawing Sheets

CONTAINER FOR THERAPEUTIC USE

FIELD OF THE INVENTION

This invention relates to a filled container with plural contents hermetically enclosed in a mutually-isolated state within compartments, and more specifically to a filled container with plural contents, which contain components susceptible to mutual reaction, hermetically enclosed therein in a mutually-isolated manner in advance, said container permitting simple and easy mixing of the plural contents without exposure to the external atmosphere upon use.

In particular, since the container permits prompt discharge of the contents at a substantially constant mixing ratio throughout, the container is suited as a deformable container filled with plural drug preparations containing components susceptible to mutual reaction, such as medical fluids for intravenous hyperalimentation (IVH) or components for elemental diet (hereinafter abbreviated "ED"), said solutions or components being useful in a closed therapy system.

DESCRIPTION OF THE RELATED ART

There is a longstanding demand for containers which permit mixing of two types of drugs or the like in a self-contained manner immediately before use. This demand is especially strong, e.g., for heating or cooling media making use of reaction heat available upon mixing of two substances or for foods or drugs many of which tend to deteriorate in nature if their ingredients or components are fed as a mixture to the production lines or are stored as a mixture over a long time.

Among these, since drugs are each composed of plural chemical substances, many of such drugs particularly tend to undergo deterioration with the passage of time if such chemical substances are subjected as a mixture to a heat-treatment step or are stored as a mixture over a long period of time. For example, medical fluids for intravenous hyperalimentation which has been increasingly practiced in recent years are, from the above-described viewpoint, one example of drug preparations which generally are unsuited to formulation into single-pack preparations. It is a basic requirement for such medical fluids for the intravenous hyperalimentation (IVH) therapy that all nutrients required for the human body be present at appropriate concentrations. Therefore, each of such medical fluids is a multi-component fluid containing glucides, amino acids, lipids, primary electrolytes, trace elements and vitamins. In view of their compatibility, their stability in production steps and the stability of the resultant medical fluid over a prolonged period of time, it is impossible under the circumstances to formulate them into a single composite solution. For example, if glucose and amino acids are combined together and fill a container as a single-pack liquid preparation, reactions such as the Maillard reaction may take place between the glucose and the amino acids during autoclave sterilization treatment or during storage so that the medical fluid may be colored or may change in quality. Further, a fat emulsion is an unstable liquid preparation. Its mixing with another infusion liquid preparation tend to develop coarsening or phase separation of fat particles. In particular, divalent metal ions which are present in an infusion liquid preparation of electrolytes are known to induce coagulation of a fat emulsion or disintegration of particles. Further, each infusion liquid preparation requires a specific appropriate pH value as an environment in which it can remain stably. Mixing of infusion liquid preparations having different appropriate pH values tends to cause turbidity or to develop precipitation.

In the case of a preparation like ED, which cannot be stored for a long time as its stability is lost when stored in a liquid form, the preparation is stored in a form separated in a powdery portion and a liquid portion. These portions are mixed together immediately before use and the resulting mixture is administered to a patient.

Home health care has attracted increasing attention in recent years. To permit easy practice of infusion and the like at home in the future, it is desired to develop a system which enables fail-free sure mixing of plural drug preparations.

Recently, a container which is filled with plural medicinal preparations has been put on the market. The container is composed of plural compartments connected together and at a connected part, is provided with isolation means through which the plural compartments can communicate with each other. Immediately before use, the isolation means is opened so that the plural medicinal preparations filling the respective compartments can be mixed in one of the compartments.

One example of a conventionally-known, therapeutic container permitting mixing of plural contents in a closed system is illustrated in FIG. 9. The container 51 of FIG. 9 is made of a deformable synthetic resin and has a first compartment 2 and a second compartment 3, which have contents stored therein and are isolated from each other. In an upper end portion of the container, a suspension hole 5 is formed to suspend the container 51. The container 51 is provided at a lower end portion thereof with discharge ports 59,57 which are in communication with the first and second compartments 2,3, respectively (as an alternative, only one discharge port can be provided in communication with one of the first and second compartments). Openable (communicable) closing means 58 is disposed in the vicinity of the lower end of an isolating portion 4 which horizontally divides the container into the first and second,compartments 2,3.

According to the conventional container 51, the closing means 58 is opened to communicate the first and second compartments 2,3 with each other, and an infusion set or the like is then connected to the discharge ports 59,57 to administer the liquid contents to a patient. Upon administration of liquid preparations to a patient, it is preferred that the mixing ratio of the liquid contents of the first compartment 2 to those of the second compartment 3 always remain constant throughout the administration, and that the discharge rate of the mixed contents should not significantly fluctuate, but this conventional container 51 can achieve neither of them due to two problems being involved therein. The first problem resides in that the mixing ratio of the liquid contents of the first compartment 2 to those of the second compartment 3 in the liquid preparation discharged through the discharge ports 59,57 does not remain constant because the communication means 56, through which the mixing of the first and second contents take place, and the discharge port 59 or 57 from which the mixture of the first and second contents is discharged are located at different positions.

Where the first compartment 2 is provided with the discharge port 59, for example, the liquid contents of the second compartment 3 are allowed to flow into the first compartment 2 through the communication means 56 and, while being mixed, the liquid contents of the first compartment 2 and those of the second compartment 3 are discharged from the first compartment 2 through the discharge port 59. Here, it is difficult to always keep constant the mixing ratio of the liquid contents of the first compartment 2 to those of the second compartment 3 throughout their discharge.

Further, since the liquid contents of the first compartment 2 and those of the second compartment 3 locally undergo mixing with each other by leading the liquid contents of the first compartment 2 to the second compartment 3 prior to their discharge as a mixture from the discharge port 59, deterioration of the mixture may start due to the two liquid contents being mixed with each other in the first compartment 2 prior to the discharge. Thus, the conventional container 51 cannot be adopted for a liquid which is reactive with another liquid (for example, solutions having different optimum pH values), especially infusion liquid preparations which are administered to a patient over a long period of time, i.e., the mixed state of the two liquids being prolonged, for example, for several hours to half a day per liter of the infusion liquid preparations.

The second problem is associated with the requirement that the container wall must have a certain degree of strength to remain durable during autoclaved sterilization. The container is therefore not fully flexible so that as the contents are discharged from the container 51, a negative pressure may arise inside the container (especially, in spaces which are generally formed at the upper end of the container for facilitating full discharge of the contents). This negative pressure then reduces the discharge rates of the contents.

The communication means 56 through which the first and second compartments 2,3 can be communicated with each other is provided at only one place in the above-exemplified container 51. As the contents are discharged from the first and second compartments 2,3, respectively, spaces are formed individually in the first and second compartments 2,3. Since these spaces are independent from each other, the pressure of one of the spaces may become more negative than that of the other space where a difference arises in size between the space in the first compartment 2 and that in the second compartment 3 or there is a difference in deformability between the first compartment 2 and the second compartment 3. This results in a reduction in the discharge rate of the contents from the one compartment. As a consequence, the mixing ratio of the contents of the first compartment to that of the second compartment can hardly remain constant from the beginning of the discharge of the contents until the end thereof.

When one of the compartments is filled with a content which is apt to be easily modified or otherwise deteriorated if oxygen is present, the contents alone is filled without air. However, a certain amount of air is filled together with the contents in the other compartment so that the contents can be discharged completely. Upon discharging the contents, it is necessary to distribute the air, which was filled in the other compartment, to both the compartments so that the contents of the first and second compartments can be discharged completely. This distribution of the air has to be performed primarily through the communication means 56 in FIG. 9, so that this distribution work is cumbersome and as a matter of fact, the air cannot be distributed well. It is accordingly difficult to completely discharge the contents from the compartments or to make constant the ratio of the discharge rate of the contents from the first compartment to that of the contents from the second compartment.

Besides the conventional container shown in FIG. 9, there is another conventional container. This container is divided into a first compartment and a second compartment, in which the second compartment has a size sufficient to store the contents of the first compartment in addition to those of the second compartment. All of the contents of the first compartment is transferred to the second compartment, in which the contents of the first compartment and those of the second compartment are mixed. The resulting liquid preparation is then administered to a patient by an infusion set or the like through a discharge port attached to the second compartment. The second compartment must therefore have a large size. This container is hence accompanied by the drawback that the container unavoidably has a large overall size. Further, the mixing operation and the discharge operation are performed separately, leading to the problem that this container can hardly permit prompt administration.

Further, since the liquid contents of the first compartment and those of the second compartment are mixed and then administered to a patient, the conventional container cannot be adopted for liquid contents which are extremely susceptible to mutual reaction or capable of stably existing only in different environments.

SUMMARY OF THE INVENTION

With the foregoing problems in view, the present invention has as a primary objective the provision of a compact, sealed self-contained mixing container for therapeutic use, which permits sterilization of plural contents, said contents containing components susceptible to mutual reaction or capable of stably existing only in different environments, storage over a prolonged period of time while maintaining them in a stable state, and at the time of use, simple, easy and prompt discharge of the contents of respective compartments while always maintaining their mixing ratio substantially constant.

More specifically, an objective of the present invention is to provide a compact container for therapeutic use, which can always discharge the contents of plural compartments at substantially a constant mixing ratio without need for gathering the contents in a single compartment and mixing them there. Another objective of the present invention is to permit simultaneously mixing and discharge of the contents and their prompt administration to a patient directly or indirectly even if the contents contain components susceptible to mutual reaction or capable of stably existing only in an environment different from each other (for example, in solutions having different pH values), so that the contents can be administered in a most stable state to the patient directly or indirectly.

To attain the above objectives, the present invention provides a therapeutic container suitable for use in a closed therapy system, said container hermetically enclosing plural contents in a mutually-isolated state and upon use, permitting discharge of the contents in a mixed state, comprising:

a) a like plural number of compartments formed within said container and each separated from another by an isolation zone provided therebetween extending from said opposite end of said container on a side of said outlet member to said one end of said container on a side of said suspending means, said compartments individually enclosing the respective contents therein;

b) suspending means formed in one end of said container; and c) an outlet member disposed at an opposite end of said container and adapted to discharge therethrough the contents, said outlet member being provided with a communication passage which is in turn equipped with openable closing means, through which communication passage said compartments are communicable, wherein upon use, said closing means is opened and said container is suspended by said suspending means, whereby the respective contents can be discharged in the mixed state through said outlet member without need for forced mixing of the contents across said respective compartments.

Preferably, the above therapeutic container further comprises a second communication passage for mutually communicating the compartments in addition to said communication passage of said outlet member, said second communication passage extending through said isolation zone at a location proximal to said suspending means and being provided with openable closing means.

BRIEF DESCRIPTION OF THE DRAWINGS

FIG. 2(*b*) is a cross-sectional view showing the closing means of the example of the communication passage, in which the closing means has been opened;

FIG. 3(*b*) is a cross-sectional view showing the closing means of the another example of the communication passage, in which the closing means has been opened;

DETAILED DESCRIPTION OF THE PREFERRED EMBODIMENTS

Figure 1:
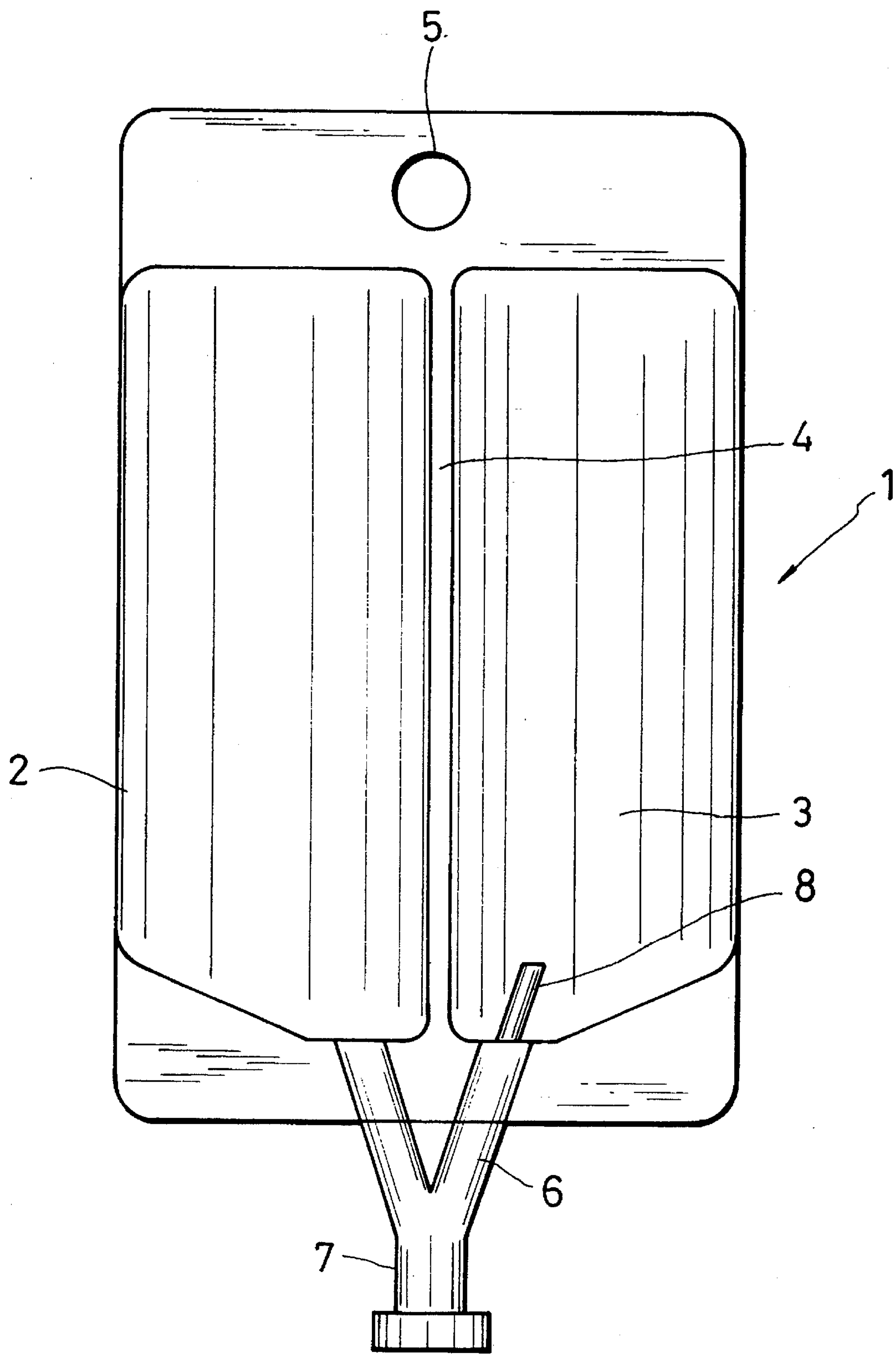
FIG. 1 is a schematic front view of a therapeutical container according to a first embodiment of the present invention, in which the therapeutic container has plural compartments.
Figure 6:
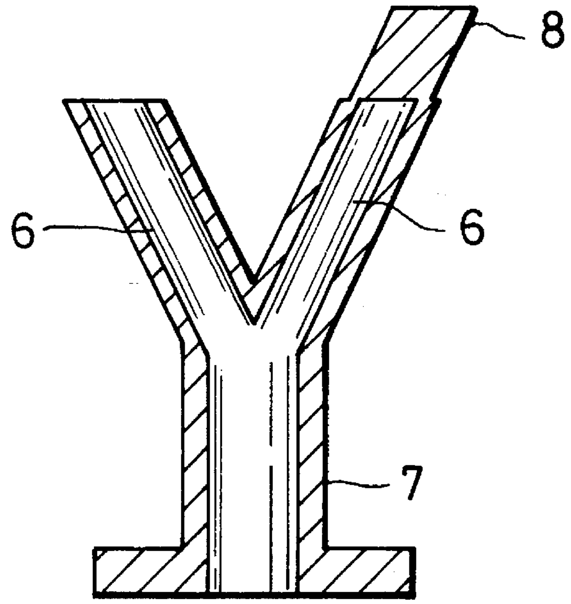
FIG. 6 is a cross-sectional view of communication passage equipped with an outlet member, which is employed in the first embodiment.

Referring first to FIG. 1, the therapeutical container according to the first embodiment of the present invention will be described. In the therapeutic container 1, a first compartment 2 and a second compartment 3—which have been formed by sealing a tubular flexible sheet along opposite end edges thereof—are connected and integrated together with an isolation zone 4 interposed therebetween. A suspension hole 5 is formed in the upper end portion of the therapeutic container 1 so that the therapeutic container 1 can be suspended from a hanger or the like. To lower end portions of the first and second compartments 2,3, a communication passage 6 is attached astride the isolation zone 4. As is illustrated in FIG. 6, the communication passage 6 is provided with an outlet member 7. The outlet member provided with the communication passage forms a Y-shape. Further, the communication passage 6 is provided with closing means 8, whereby the communication passage connecting the first compartment 2 and the second compartment 3 with each other, is blocked. In this embodiment, the communication passage is provided with the closing means on a side of the second compartment 3. The closing means can, however, be provided on a side of the first compartment 2.

An infusion set or the like is connected to the outlet member 7. Immediately before use, the closing means 8 is broken off to open the communication passage by an operation from the outside of the container. The container is suspended from a hanger by hooking it at the suspension hole 5 on the hanger. A content of the first compartment 2 and a content of the second compartment 3 are then discharged through the outlet member 7 while being mixed together at the same time. These contents can be discharged and promptly administered to a patient directly or indirectly at a substantially constant mixing ratio from the beginning of the discharge until the end thereof.

Although the therapeutic container 1 in FIG. 1 has two compartments, the number of compartments can be determined depending on the kinds of contents and can be set as desired. The container according to the present invention can function irrespective of the number of compartments insofar as the container is provided with at least two compartments.

Where the container according to the present invention is equipped, for example, with three compartments vertically defined by isolation zones therebetween, such container can be constructed in a similar way to that equipped with two compartments, by using a trifurcated communication passage (instead of a bifurcated communication passage for two compartments) leading to a common outlet mouth, two of which are equipped with closing means. The container can be constructed likewise when four or more compartments are provided.

Although contents to be stored in the compartments will be described subsequently, the contents are not limited to therapeutic preparations but contents susceptible to mutual reaction can be stored appropriately. In particular, application of the present invention to liquid preparation bags for therapeutic use is expected to be effective not only in preventing modification or deterioration of the contents upon autoclaved sterilization or with the passage of time but also in avoiding bacterial contamination upon mixing the therapeutic liquid preparations in a hospital. Further, the adoption of a fabrication process which will be described subsequently herein can easily improve the interior cleanliness of the bag, that is, the container. The application of the present invention to medicinal liquid preparation bags is therefore considered to bring about effects of the present invention to the greatest extent.

Figure 2A:
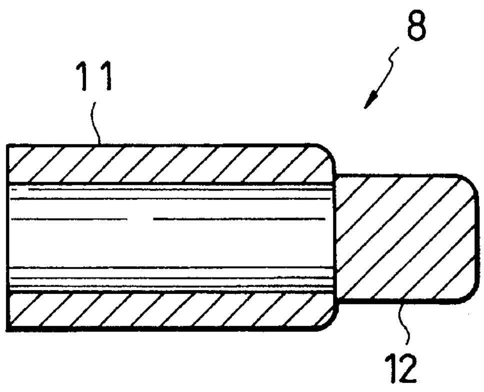
FIG. 2(*a*) is a cross-sectional view of one example of an openable closing means provided on a communication passage.
Figure 2B:
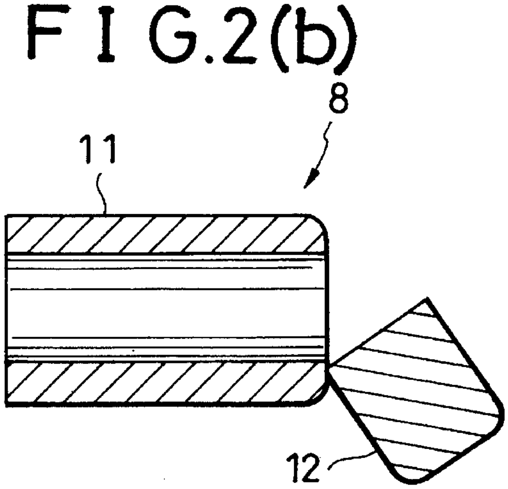
Figure 3A:
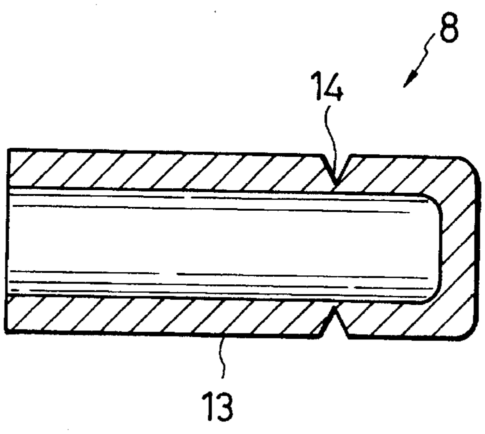
FIG. 3(*a*) is a cross-sectional view of another example of the openable closing means provided on the communication passage.
Figure 3B:
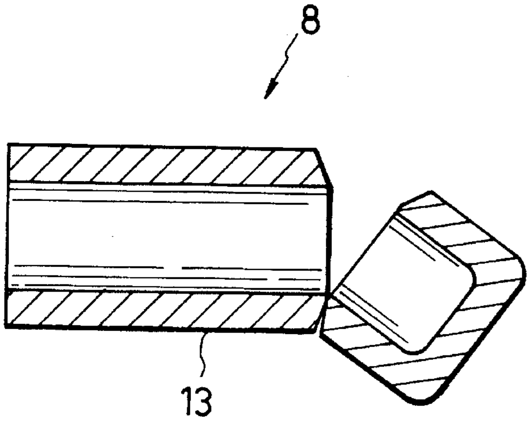

The closing means 8 can take various forms. The specific form of one example of the closing means is illustrated in FIG. 2(*a*), in which the closing means 8 is composed of a tube portion 11 and a plug portion 12 and a passage in the tube portion 11 can be opened by breaking off the plug portion 12. The closing means 8 in this state is depicted in FIG. 2(*b*). Further, the specific form of another example of the closing means is shown in FIG. 3(*a*), in which a tube 13 is provided with a thin-walled portion 14. By an operation from the outside of the container, the tube 13 is broken off at the thin-walled portion 14 so that a passage in the tube 13 can be opened. The closing means 8 in this state is illustrated in FIG. 3(*b*). Various other forms are conceivable for the closing means 8. Any structure can be employed as long as it is openable by an operation from the outside of the container.

Figure 4:
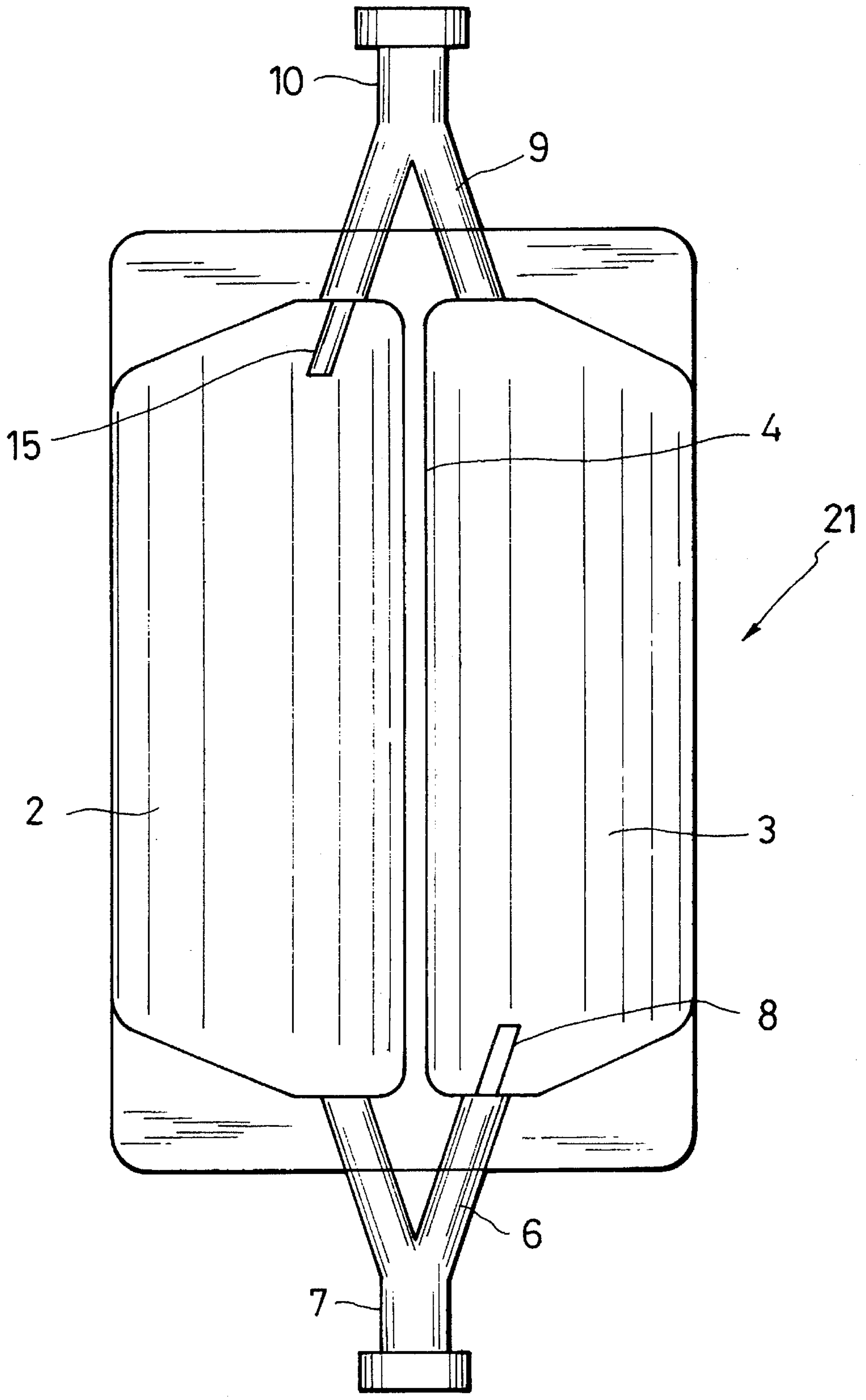
FIG. 4 is a schematic front view of a therapeutical container according to a second embodiment of the present invention, in which the therapeutic container has plural compartments.

Referring next to FIG. 4, the therapeutic container according to the second embodiment of the present invention will be described. In the therapeutic container 21, a first compartment 2 and a second compartment 3—which have been formed by sealing a tubular flexible sheet along opposite end edges thereof—are connected and integrated together with an isolation zone 4 interposed therebetween. The therapeutic container 21 is provided at one end thereof with a first Y-shaped communication passage 6 which can connect the first compartment 2 and the second compartment 3 with each other. The therapeutic container 21 is provided at an opposite end with a second Y-shaped communication passage 9 which can also connect the first compartment 2 and the second compartment 3 with each other. Further, the first communication passage 6 and the second communication passage 9 are provided with an outlet member 7 and an outlet member 10, respectively. In addition, the first communication passage 6 is provided on a side of the second compartment with closing means 8 while the second communication passage 9 is provided on a side of the first compartment 2 with closing means 15. A passage in each communication passage is therefore blocked so that the first compartment 2 and the second compartment 3 are completely isolated.

Contents can be poured into the first compartment through the outlet member 7 of the therapeutic container 21, whereas other contents can be poured into the second compartment 3 through the outlet member 10. To administer the contents of the therapeutic container 21 to a patient, the closing means 8 and the closing means 15 are first opened, followed by the connection of an infusion set or the like to the outlet member 7 or the outlet member 10. To pour a further medicinal liquid preparation into the therapeutic container 21, the further medicinal liquid preparation can be readily poured through the outlet member 7 or the outlet member 10 to which the infusion set or the like is not connected. Described specifically, the therapeutic container 21 is symmetrical with respect to a transverse center line. When an infusion set is connected, for example, to the outlet member 7 to use it as a discharge port, the outlet member 10 can be used as a pouring and mixing port. The first communication passage 6 or the second communication passage 9 can be hooked as suspending means on a hanger or the like, so that the therapeutic container 21 can be used in a suspended state.

If only the closing means 8 is opened (that is, the closing means 15 is not opened) in the therapeutic container 21 shown in FIG. 4, the therapeutic container 21 can be used by a similar operation to the therapeutic container 1 depicted in FIG. 1. When both the closing means 8 and 15 are opened as described above upon use, the closing means 15 functions as a second communication passage so that the first compartment 2 and the second compartment 3 are also communicated with each other in the upper part of the container 21 (when suspended). When the therapeutic container 21 is suspended, a space above the contents in the first compartment 2 and a space above the contents in the second compartment 2 are connected through the closing means 15 (the communication passage 9) so that the liquid levels of the liquid contents in the first and second compartments 2,3 easily have the same height. Further, the spaces above the respective contents, said spaces affecting the discharge rates of the contents of the first and second compartments 2,3, are connected through the communication passage 9 so that the air in one of the spaces can freely flow into the other space and vice versa to equalize the pressure in the spaces. The discharge rates of the contents are therefore not affected even if the therapeutic container is not easily deformed due to the differences in their flexibilities and/or shape. As a consequence, the ratio of the discharge rate of the contents of the first compartment 2 to that of the contents of the second compartment 3 always remains substantially constant from the beginning of the discharge until the end thereof. In addition, the therapeutic container 21 is fabricated in such a way that the ratio of the transverse width of the first compartment 2 to that of the second compartment 3 always has a constant value when measured at a given equal liquid level. By designing the therapeutic container in this manner, the ratio of the amount of the liquid contents of the first compartment flowing into the outlet member 7 to the amount of the liquid contents of the second compartment flowing into the outlet member 7 always remains at a substantially constant value from the beginning of the discharge until the end thereof, so that the contents of the first compartment 2 and those of the second compartment 3 are always mixed and administered at a substantially constant mixing ratio to the patient.

Figure 5:
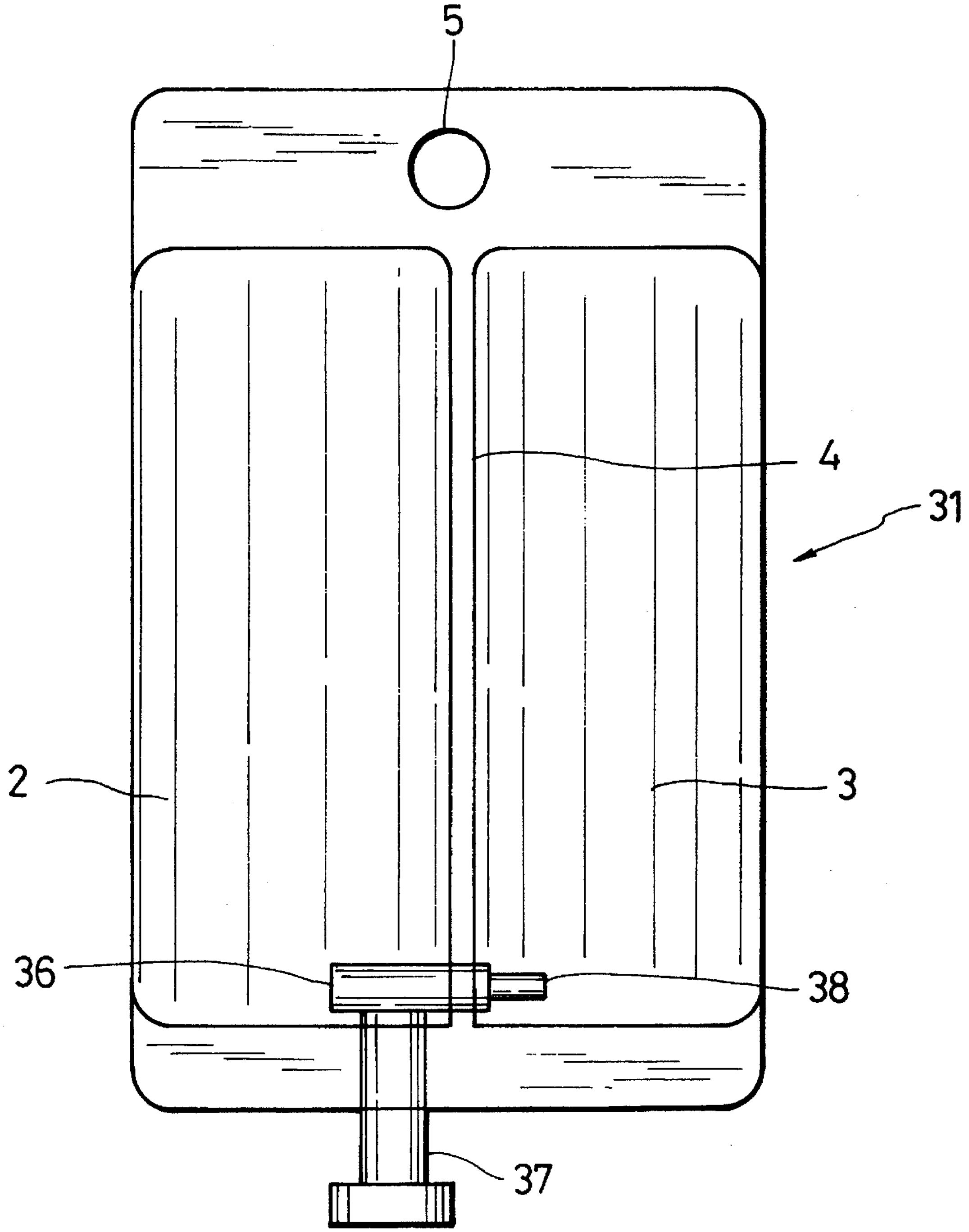
FIG. 5 is a schematic front view of a therapeutical container according to a third embodiment of the present invention, in which the therapeutic container has plural compartments.
Figure 7:
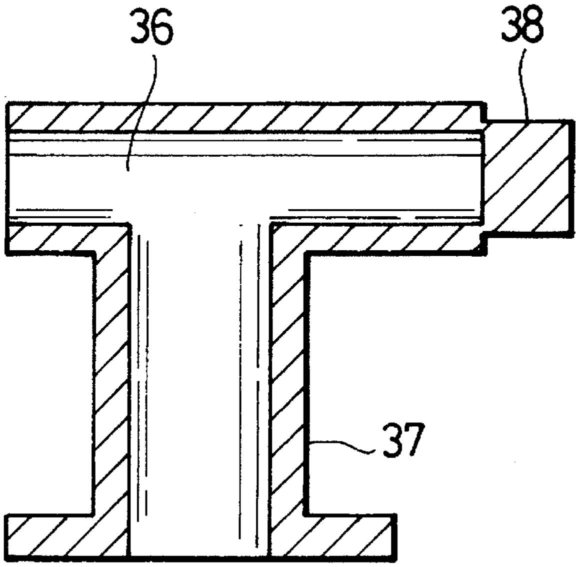
FIG. 7 is a cross-sectional view of communication passage equipped with an outlet member, which is employed in the third embodiment.

The therapeutic container according to the third embodiment of the present invention will next be described with reference to FIG. 5. It has substantially the same basic structure as the first embodiment shown in FIG. 1. A difference is, however, found in that a communication passage 36 adapted to communicate a first compartment 2 and a second compartment 3 with each other in the therapeutic container 31 is arranged inside the container and extends through an isolation zone 4. In other words, the communication passage 36 is located inside the first compartment 2 and the second compartment 3. As is depicted in FIG. 7, an outlet member 37 forming a T-shape is provided with the communication passage 36 and is located at an end portion of the container. Further, the communication passage 36 is provided at an end portion on a side of the second compartment 3 with closing means 38, whereby the first compartment 2 and the second compartment 3 are surely isolated from each other.

Figure 9:
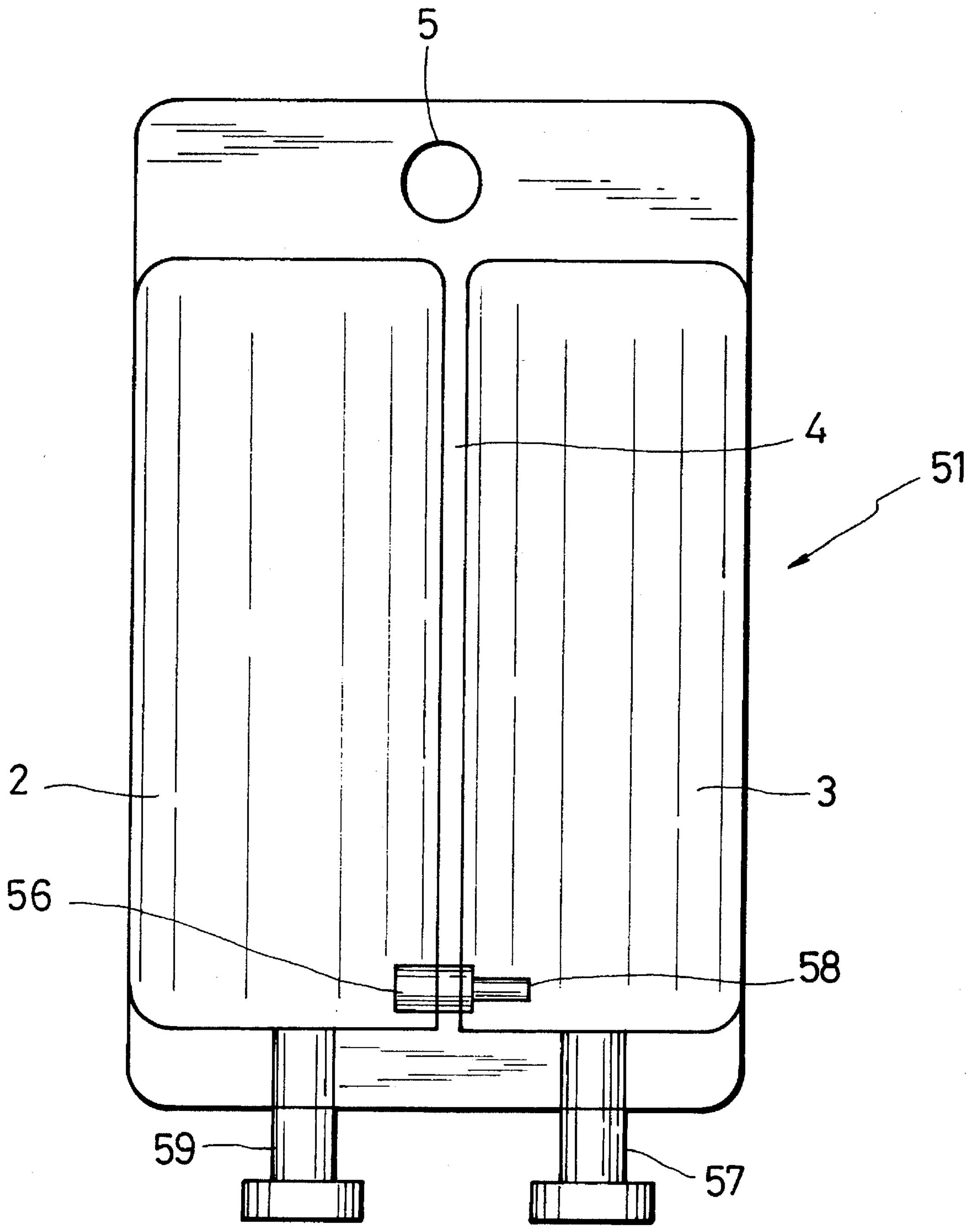
FIG.9 PRIOR ART
FIG. 9 is a schematic front view of a conventional therapeutic container.

In the therapeutic container 31, the first compartment 2 and the second compartment 3 can be communicated with each other by opening the closing means 38 by an operation from the outside of the container. At this time, the liquid contents of the first compartment 2 and those of the second compartment 3 are allowed to be naturally and locally mixed with each other through communication passage 36, but they can not be fully mixed unless the discharge of the contents starts. Comparing the container of FIG. 5 according to the present invention with the conventional container depicted in FIG. 9, since the communication passage 56 and the outlet member 59 of the conventional container shown in FIG. 9 are each located at a different position, discharge of the liquid contents occurs subsequent to their partial mixing in the first compartment 2. As the liquid contents partially mixed in the first compartment 2 are discharged through the outlet member 59, the liquid contents in the second compartment 3 flow into the first compartment 2 so that the liquid contents of the first compartment 2 and those of the second compartment 3 are mixed together in the first compartment 2 at a position near the communication passage 56. However, the mixed liquid contents and the unmixed liquid contents of the first compartment 2 are non-uniformly drawn into and discharged through the outlet member 59. It has hence been difficult to achieve and maintain a constant mixing ratio. In contrast, the therapeutic container 31 shown in FIG. 5 according to the present invention is not constructed in such a way that the liquid contents of the second compartment 3 are caused to flow into the first compartment 2 and the respective liquid contents are mixed within the first compartment 2. The liquid contents of the first compartment 2 are discharged through the communication passage 36 and then through the outlet member 37, and the liquid contents of the second compartment 3 are discharged similarly through the communication passage 36 and then through the outlet member 37. Namely, the respective liquid contents contact each other in the communication passage 36 and are mixed in the outlet member 37 and then discharged. Since the liquid contents of the first compartment 2 and those of the second compartment 3 are always allowed to flow at a substantially constant ratio into the outlet member 37, so that the mixing ratio of the respective contents discharged from the outlet member 37 always remains substantially constant.

Figure 8:
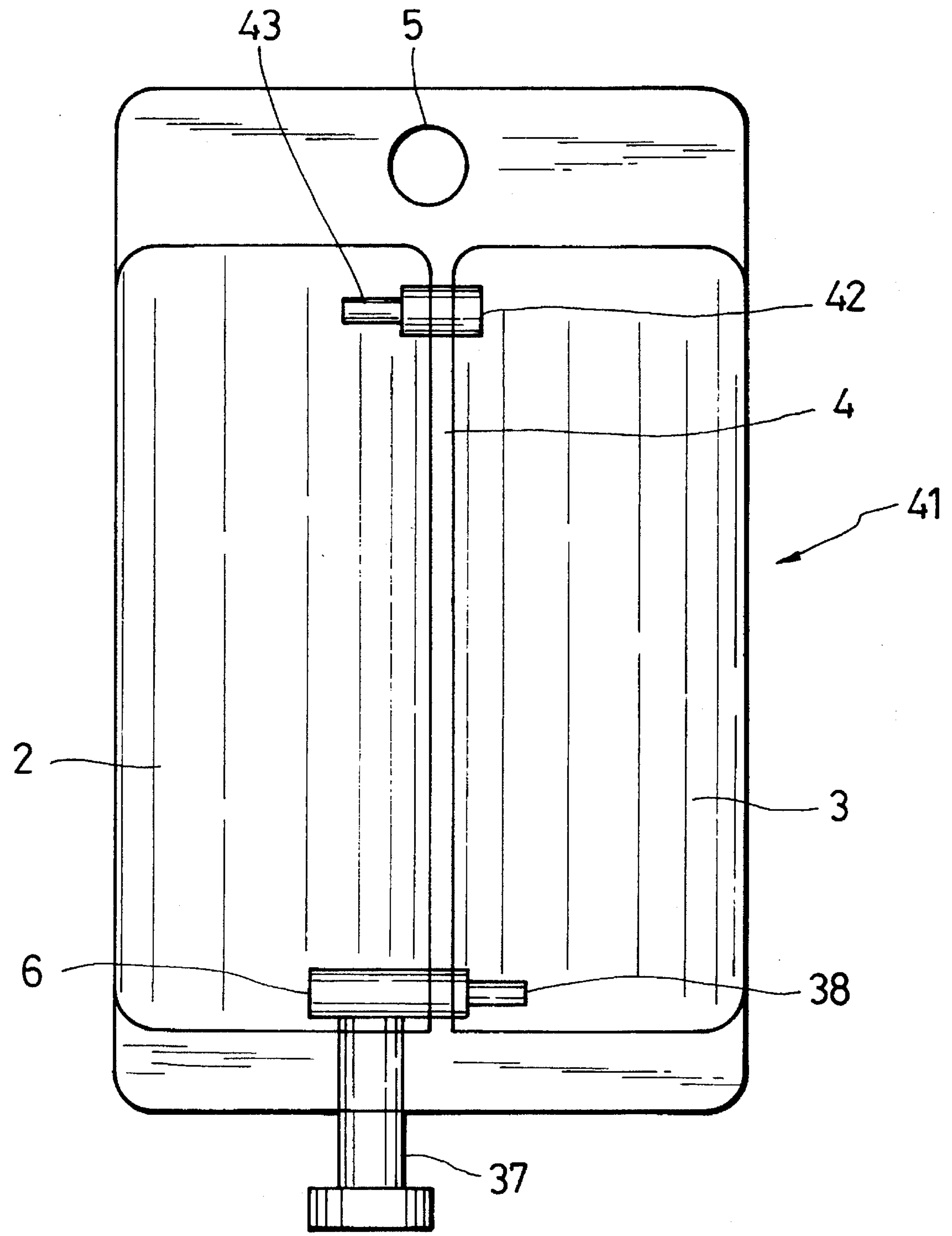
FIG. 8 is a schematic front view of a therapeutical container according to a fourth embodiment of the present invention, in which the therapeutic container has plural compartments.

To ensure a constant mixing ratio for the discharged liquid contents consistently from the beginning of the discharge to the end thereof, it is preferred to provide another communication passage on a side opposite to the outlet member as illustrated in FIG. 8 as the fourth embodiment of the present invention. Accordingly, the therapeutic container 41 according to the fourth embodiment of the present invention is provided with a second communication passage 42 in addition to the first communication passage 36. Although the second communication passage 42 is arranged extending through the isolation zone 4 like the first communication passage 36, this second communication passage 42 may take the form of the Y-shape depicted in FIG. 4. Immediately before use, the closing means 38 and closing means 43 are opened. When the therapeutic container 41 is suspended by hooking it at the suspension hole 5 on a hanger after the opening of the first and second communication passage 36,42, the liquid level of the liquid contents in the first compartment 2 and that of the liquid contents in the second compartment 3 are located at the same height. In addition, the therapeutic container 41 is fabricated in such a way that the ratio of the transverse width of the first compartment 2 to that of the second compartment 3 always has a constant value when measured at a given equal liquid level. By designing the therapeutic container in this manner, the ratio of the amount of the liquid contents flowing from the first compartment 2 into the outlet member 37 to the amount of the liquid contents flowing from the second compartment 3 into the outlet member 37 always remains at a constant value from the beginning of the discharge until the end thereof, so that the contents of the first compartment 2 and those of the second compartment 3 are always mixed and administered at a substantially constant ratio to a patient.

In the therapeutic container 41, it is possible to fill the first compartment 2 with liquid contents and the second compartment 3 with powdery contents. The closing means 38,43 are opened so that a part of the liquid content is allowed to move from the first compartment 2 into the second compartment 3. The liquid contents so move then dissolve the powdery contents in the second compartment 3. Thereafter, the resulting mixture can be administered in a similar manner to the method described above.

These effects and advantages have been described in detail with respect to the third embodiment and the fourth embodiment. Needless to say, similar effects and advantages are available from the other embodiments.

A description will next be made of a process for the fabrication of a container according to the present invention by taking as an example the container 1 illustrated in FIG. 1. A tubular plastic sheet of desired length and flat width is heat-sealed partially at opposite end openings thereof (a portion for the communication passage 6 and a portion for inserting a nozzle for introducing the contents remain unsealed) and a part corresponding to the isolation zone 4, whereby the first compartment 2 and the second compartment 3 are substantially formed. A molding of the closing means 8, which has been formed by injection molding, is welded to one of bifurcated portions of the communication passage 6 which has also been formed separately by injection molding and has the outlet member 7. The resulting sub-assembly is then welded to the heat-sealed tubular plastic sheet so that one of the bifurcated portions, which is provided with the closing means 8, is connected to the second compartment 3 with the closing means 8 located inside the second compartment 3 and the other bifurcated portion of the communication passage 6 is connected to the first compartment 2, whereby the container 1 is completed.

The contents can be filled and sealed in the first and second compartments 2,3, respectively, by filling the first compartment 2 with the contents through the outlet member 7, plugging the outlet member 7 with a rubber stopper or the like, filling the second compartment 3 with the other contents using a nozzle through an elongated portion remaining unsealed in the sealed part on the side of the suspension hole 5, and sealing the elongated unsealed portion. Alternatively, both the contents can be introduced in the respective compartments through nozzles.

To fabricate a container equipped with two communication passages, for example, the container 21 depicted in FIG. 4, a molding of the closing means 8, which has been formed by injection molding, is welded to the communication passage 6 which has also been formed separately by injection molding and has the outlet member 7. The resulting sub-assembly is then welded to one end of a partially-sealed (heat-sealed) tubular plastic sheet which has been formed as described above and defines the first and second compartments 2,3 with the isolation zone 4 interposed therebetween. Further, another sub-assembly, which is composed of the second communication passage 9 formed by injection molding and the outlet member 10 and the closing means 15 also formed separately by injection molding and welded to the second communication passage 9, is welded to an opposite end of the partially sealed (heat-sealed) tubular plastic sheet.

The contents can be filled and sealed in the first and second compartments 2,3, respectively, by filling the first compartment 2 with the contents through the outlet member 7, plugging the outlet member 7 with a rubber stopper or the like, filling the second compartment 3 with the other contants through the outlet member 10, and plugging the outlet member 10 with a rubber stopper or the like.

In each of the fabrication processes described above, the blow-film tubular plastic sheets were used. As an alternative, it is also possible to use a pair of rectangular plastic sheets heat-sealed on the sides thereof.

As long as the fabrication process is concerned, no limitation is practically imposed on the material of such plastic sheets. Any resin suited for the application purpose of the container can be chosen, such as a modified polyolefin resin or a polyester resin, to say nothing of a polyolefin resin which features high safety and low price.

These plastic sheets can be formed by blow-film extrusion, calendering, T-die extrusion or the like. By such a forming method, the plastic sheets can be provided in either a single-layer form or a multilayer form.

A description will next be made of contents to be stored in the container. The contents suited for storage in the container contain components, respectively, which are susceptible to mutual reaction. The term "susceptible to mutual reaction" as used herein means primarily that a chemical substance tends to undergo a chemical reaction with another chemical substance when they contact each other. Illustrative of substances susceptible to mutual reaction include glucose and amino acids, aqueous solvents and various vitamins, starch/proteins and various enzymes, metal ions and chelating agents, unsaturated fatty acids, metal ions and enzymes, acids and alkalis, aqueous solvents and salts, as well as aqueous solvents and antibiotics or anticancer agents. Illustrative of reactions which may take place include the Maillard reaction, hydrolysis, oxidation, reduction, and various enzymatic reactions.

According to the present invention, plural contents in a container can be administered at a constant mixing ratio to a patient without full mixing of these contents within the container. Further, it is no longer required to gather the contents of individual compartments into a single compartment and then to mix them there. This has made it possible to reduce the overall size of the container. With the foregoing in view, specific examples of contents suited for containers according to this invention include an intravenous hyperalimentation (IVH) base solution or a hypertonic glucose solution and an amino acid solution, which are employed as an IVH solution in IVH therapy, as well as a powdery medicinal preparation and a solution in an elemental diet (ED). The components of these contents are prone to modification or discoloration when thermally sterilized as single-pack liquid preparations or are susceptible to similar modification when stored as single-pack liquid preparations. Further, if their mixing is not performed in a closed system, problems such as a dispensing error and contamination tend to occur.

The above advantages of the present invention have been confirmed by the following experiment. Using a linear low-density polyethylene resin, a blown film of 250 mm in flat width and 0.25 mm in thickness was produced by blow-film extrusion. The blown film was cut at a desired length and, as illustrated in FIG. 1, the partial end seals and the isolation zone 4 were formed by heat-sealing the blown film. Extra portions such as outer margins of the end seals and the portion corresponding to the suspension hole 5 were cut off. In addition, moldings of the communication passage 6, which had the outlet member 7, and of the closing means 8 shown in FIG. 1 were formed from a linear low-density polyethylene by injection molding. The closing means 8 was welded to the communication passage 6 to form a sub-assembly. The sub-assembly was then welded to the blown film whose opposite ends had been partially sealed, whereby the therapeutic container 1 was produced.

Next, a blown film produced as in a similar manner was heat-sealed to form partial end seals and the isolation zone 4 as illustrated in FIG. 4. Formed next from linear low-density polyethylene by injection molding were moldings of the first communication passage 6, which had the outlet member 7, and of the closing means 8, and other moldings of the second communication passage 9, which had the outlet member 10, and of the closing means 15, all shown in FIG. 4. A sub-assembly formed of the first communication passage 6 and the closing means 8 welded thereto was welded to one end of the blown film which was partially sealed at the opposite ends thereof. Further, another sub-assembly formed of the second communication passage 9 and the closing means 15 welded thereto was welded to the opposite end of the blown film partially sealed. The therapeutic container 21 was hence fabricated.

In a similar manner, the conventional container 51 shown in FIG. 9 was next fabricated.

In each of the therapeutic containers 1 (FIG. 1), 21 (FIG. 4) and 51 (FIG. 9), the first compartment was filled with 600 ml of an IVH base solution whereas the second compartment was filled with 300 ml of an amino acid transfusion solution through the outlet member(s) on a nozzle inserted in an unsealed portion of the end seal(s). Before the filling, the amino acid infusion solution had been added with a colorant so that the amino acid infusion solution had been colored. The therapeutic containers 1,21,51 so filled were subjected to autoclaved sterilization at 110° C. for 40 minutes. By an operation from the outside of each container, the closing means for the communication passage was or were broken. The filled therapeutic container was then suspended from an irrigator stand and an infusion set was connected to the outlet member. Variations in the concentration of the colorant in the medicinal solution, which was discharged from the infusion set, were observed from the beginning of the discharge until the end thereof. As a result, the concentration of the colorant in the liquid preparation remained substantially constant from the beginning of the discharge until the end of the discharge in the therapeutic container 1 and therapeutic container 21. In the case of the conventional therapeutic container 51, on the other hand, the concentration of the colorant in the medicinal preparation discharged around the beginning of the discharge was low but the concentration of the colorant in the medicinal preparation discharged around the end of the discharge become higher.

What is claimed is:

1. A therapeutic container suitable for use in a closed therapy system, said container hermetically enclosing plural contents in a mutually-isolated state and upon use, permitting discharge of the contents in a mixed state, the therapeutic container comprising:

suspending means formed in one end of said container;

an outlet member disposed at an opposite end of said container and adapted to discharge said contents;

a plural number of compartments formed within said container, each of said compartments being separated from one another by an isolation zone provided therebetween, said isolation zone extending from said one end of said container to said opposite end of said container, said compartments individually enclosing said respective contents therein;

a first communication passage formed within said outlet member and communicated with said respective compartments, said first communication passage being equipped with first openable closing means, through which said outlet member and said compartments are communicable; and a second communication passage arranged at a location proximal to said suspending means and communicated with said respective compartments, said second communication passage being provided with second openable closing means, through which said second communication passage and said compartments are communicable;

wherein upon use, at least one of said first and second closing means is opened and said container is suspended by said suspending means, whereby the respective contents can be discharged in the mixed state through said outlet member.

2. A therapeutic container according to claim 1, wherein said second communication passage is arranged to extend on both sides of said isolation zone.

3. A therapeutic container according to claim 2, wherein the number of said compartments divided by said isolation zone is two, and said second communication passage has a Y-shape and is used as the suspending means.

4. A therapeutic container according to claim 3, wherein said first closing means of said first communication passage of said outlet member and said second closing means of said second communication passage are arranged in different ones of said compartments, respectively.

5. A therapeutic container according to claim 1, wherein said second communication passage extends through said isolation zone.

6. A therapeutic container according to claim 1, wherein the respective compartments divided by said isolation zone have the same transverse area when measured at a given equal liquid level in said respective compartments of said container in the suspended state.

* * * * *